(12) United States Patent
Padin et al.

(10) Patent No.: US 6,215,037 B1
(45) Date of Patent: Apr. 10, 2001

(54) METHOD FOR SELECTIVE ADSORPTION OF DIENES

(75) Inventors: Joel Padin, Ann Arbor, MI (US); Curtis L. Munson, Oakland, CA (US); Ralph T. Yang, Ann Arbor, MI (US)

(73) Assignees: The Regents of the University of Michigan, Ann Arbor, MI (US); Chevron U.S.A., San Francisco, CA (US)

( * ) Notice: Subject to any disclaimer, the term of this patent is extended or adjusted under 35 U.S.C. 154(b) by 0 days.

(21) Appl. No.: 09/179,667

(22) Filed: Oct. 27, 1998

(51) Int. Cl.[7] .............................. C07C 7/00; C07C 7/12; C10C 3/00
(52) U.S. Cl. .................. 585/809; 585/810; 585/820; 585/829; 210/660; 210/690; 208/310 Z
(58) Field of Search ..................... 585/809, 810, 585/820, 829; 210/660, 690; 208/310 Z

(56) References Cited

U.S. PATENT DOCUMENTS

| | | | |
|---|---|---|---|
| 2,882,243 | 4/1959 | Milton | 252/455 |
| 2,882,244 | 4/1959 | Milton | 252/455 |
| 3,130,007 | 4/1964 | Breck | 23/113 |
| 3,221,073 | * 11/1965 | Davis et al. | 260/677 |
| 3,311,671 | * 3/1967 | Baker | 260/677 |
| 3,331,882 | * 7/1967 | Mattox | 260/677 |
| 3,350,472 | 10/1967 | DeFeo | 260/677 |
| 3,785,122 | 1/1974 | Yatsurugi et al. | 55/75 |
| 3,992,471 | 11/1976 | Priegnitz | 260/681.5 R |
| 4,019,880 | 4/1977 | Rabo et al. | 55/68 |
| 4,717,398 | 1/1988 | Pearce | 55/58 |
| 4,917,711 | 4/1990 | Xie et al. | 55/68 |
| 5,268,023 | 12/1993 | Kirner | 95/103 |
| 5,365,011 | 11/1994 | Ramachandran et al. | 585/829 |
| 5,551,257 | 9/1996 | Jain | 62/644 |
| 5,554,208 | 9/1996 | Mullhaupt et al. | 95/96 |
| 5,656,064 | 8/1997 | Golden et al. | 95/96 |
| 5,672,196 | 9/1997 | Acharya et al. | 95/97 |
| 5,675,052 | 10/1997 | Menon et al. | 585/717 |
| 5,713,984 | 2/1998 | Monnot et al. | 95/100 |
| 5,744,687 | 4/1998 | Ramachandran et al. | 585/829 |

FOREIGN PATENT DOCUMENTS

| | | |
|---|---|---|
| 1356420 | 6/1974 | (GB) . |
| 1509586 | * 5/1978 | (GB) . |

OTHER PUBLICATIONS

"Olefin/Paraffin Separations by Adsorption: π–Complexation vs. Kinetic Separation" Salil U. Rege, Joel Padin, and Ralph T. Yang, AIChE Journal, Apr. 1998, vol. 44, No. 4, pp. 799–809.

"*Separations* Modification of Resin–Type Adsorbents for Ethane/Ethylene Separation," Zhongbiao Wu, Sang–Sup Han, Soon–Haeng Cho, Jong–Nam Kim, Kuck–Tack Chue, and Ralph T. Yang, Ind. Eng. Chem. Res. 1997, 36, 2749–2756.

"Gas Separation and Purification by Polymeric Adsorbents: Flue Gas Desulfurization and $SO_2$ Recovery with Styrenic Polymers", E.S. Kikkinides and R.T. Yang, Ind. Eng. Chem. Res. 1993, 32, 2365–2372.

"*Materials and Interfaces Ab Initio* Molecular Orbital Study of Adsorption of Oxygen, Nitrogen and Ethylene on Silver–Zeolite and Silver Halides", N. Chen and R.T. Yang, Ind. Eng. Chem. Res. 1996, 35, 4020–4027.

"New Sorbents for Olefin/Paraffin Separations by Adsorption via π–Complexation", R.T. Yang and E.S. Kikkinides, AIChE Journal, Mar. 1995, vol. 41, No. 3, pp. 509–517.

"Spontaneous Monolayer Dispersion of Oxides and Salts onto Surfaces of Supports: Applications to Heterogeneous Catalysis", You–Chang Xie and You–Qi Tang, Advances in Catalysis, vol. 37, pp. 1–43.

International Search report dated Jan. 21, 2000 for Int'l Application No. PCT/US 99/23042.

* cited by examiner

*Primary Examiner*—Walter D. Griffin
*Assistant Examiner*—Tam M. Nguyen
(74) *Attorney, Agent, or Firm*—Young & Basile, P.C.

(57) ABSTRACT

The invention provides specific adsorbents and methods for separating an unsaturated hydrocarbon from a mixture containing such hydrocarbon. The adsorbents and methods are useful for separating dienes from mono-olefins.

26 Claims, 6 Drawing Sheets

METHOD FOR SELECTIVE ADSORPTION OF DIENES

FIELD OF THE INVENTION

The present invention relates to a process, and specifically selected adsorbents, for selective adsorption to separate a diene from a mixture, particularly one containing mono-olefin.

BACKGROUND OF THE INVENTION

In the preparation of commercial hydrocarbon product, it is often necessary to separate the desired product from other hydrocarbons having similar boiling points. For example, butene is synthesized commercially by processes which yield butadiene mixed with 1-butene. Conversely, butadiene product may also be contaminated with butene. Depending on the process used, the mixture may include other $C_3$ and $C_4$ hydrocarbon components including but not limited to 2-butene, other n-butenes, n-butane, isobutane, and isobutylene.

Purifying the mono-olefin, 1-butene, is particularly troublesome due to the closeness of its boiling point to that of 1,3-butadiene. In order to increase the purity of 1-butene, it is necessary to separate it from other hydrocarbons. Ordinarily, fractionation alone is incapable of completely separating 1,3-butadiene to achieve the desired purity of 1-butene in these mixtures. Presently, butadiene is separated from olefins and paraffins primarily by distillation with selective solvents and by absorption using solutions of absorbents. Extractive distillation is relatively energy-intensive, complex and not economical. Selective absorption with metal salt solution involves a significant number of stages with recycling of streams between stages. This method has the disadvantage of being energy-intensive and requiring handling and recirculating of solvent streams which themselves contain contaminants or are subject to degradation. Current processes for olefin/paraffin separation have not been sufficiently selective to economically achieve the desired result for purifying mixtures of unsaturated hydrocarbons. Therefore, there remains the need for an improved method and improved adsorbents for use in methods to effectively and economically purify unsaturated hydrocarbons.

SUMMARY OF THE INVENTION

The invention provides new methods for separating unsaturated hydrocarbons from a mixture comprising the unsaturated hydrocarbons. The invention provides adsorbents specifically selected for accomplishing the separation. The adsorbents and separation methods are particularly useful for selective adsorption of a diene from mixtures containing the diene; and are very effective for separating dienes from mono-olefins. In one aspect the invention provides methods and adsorbents to separate butadiene, hexadiene and/or octadiene from hydrocarbon mixtures; particularly where the hydrocarbon mixture contains a mono-olefin such as butene, hexene and/or octene.

Diene and mono-olefin compounds are often found together as a result of industrial processing. The separation of dienes from mono-olefin is difficult to achieve due to the closeness of their respective boiling points. This difficulty is illustrated by considering 1,3-butadiene, which has a boiling point of −4.4° C. and 1-butene which has a boiling point of −6.3° C.

The invention in one aspect, is particularly suited to cause such separation. Other important diene\mono-olefin separations include separation of hexadiene from hexene and separation of octadiene from octene. In the process of the invention, the diene is separated from a mixture comprising the diene by contacting the mixture with an adsorbent which preferentially adsorbs the diene. This produces a non-adsorbed component and a diene-rich adsorbed component.

In one aspect, the adsorbent comprises an ion-exchanged zeolite X, zeolite Y, and/or zeolite LSX. The selected zeolite has exchangeable cationic sites, with silver cation or copper cation present at some or all of the exchangeable cationic sites. Substantial cation exchange is preferred so that at least half of the cationic sites of the ion exchange zeolite contain a copper or silver cation. It is preferred that the ion exchange be substantially or essentially complete so that the silver or copper ion exchange level of the exchangeable ion content is substantial enough to change the adsorption characteristic. In the case of the silver ion-exchanged zeolite, desirably a silver ion exchange level of the exchangeable ion content is at least 70%, more desirably at least 80%, most desirably at least 85%, preferably at least 90% and more preferably at least 95%. Most preferably, substantially all (i.e., 99%) of the exchangeable ion sites are occupied by silver cations. Alternatively, the X-zeolite, Y-zeolite or zeolite LSX is a copper ion-exchanged zeolite. It is preferred that the ion exchange be as complete as described immediately above with respect to the silver cation. That is, at least half of the cationic sites of the copper ion exchanged zeolite are occupied by copper. In the case of copper ion-exchanged zeolite, the same level of high exchange content applies, according to the progressive levels stated above for silver. It is preferred that essentially complete ion exchange occur whereby substantially all (i.e., 99%) of the exchangeable cationic sites are occupied by copper cations.

The copper and silver ion exchanged zeolites provide a unique advantage in that diene\/mono-olefin separation is facilitated by formation of π-complexation bonds. Therefore, the silver ion exchanged zeolite, when used as adsorbents, have the unique ability to form π-complexation bonds for releasibly retaining the targeted unsaturated hydrocarbon desired to be selectively removed. By formation of π-complexation bond, the silver or copper ion exchange zeolite is able to retain the targeted unsaturated hydrocarbon at a selected temperature and pressure. Thereafter, the silver or copper ion-exchanged zeolite releases the adsorbed targeted hydrocarbon when either or both of temperature and pressure are changed to cause desorption (release).

In another aspect, separation of a targeted unsaturated hydrocarbon compound is achieved by contacting a mixture containing the targeted compound with an adsorbent which comprises a type A zeolite. The type-A zeolite is usable in its calcium form. The type A zeolite may also be used for selective adsorption where metal cations selected from the group of alkaline metal cation and alkaline earth metal cation are present. Therefore, the Type-A zeolite may be represented by the nominal general formula $M^{+1}_x Z^{+2}_y A^{+3}_b$ $[(AlO_2)_{12}(SiO_2)_{12}]$ wherein $M^{+1}$ is an alkali cation, $Z^{+2}$ is an alkaline earth cation, and $A^{+3}$ is a tri-valent cation, the value of x is 0 to 12, the value of y is 0 to 6, and the value of b is at minimum zero and at maximum less than the sum of x plus y, provided that: x+2y+3b is 12. For charge balance, the maximum value of b is 4. It is preferred that b is less than 4. The alkaline metal cation is selected from lithium, sodium, potassium, rubidium and cesium and mixtures thereof and the alkaline earth metal cation is selected from the group consisting of beryllium, magnesium, calcium, strontium, barium and mixtures thereof. The trivalent cation is preferably a metal compound capable of a trivalent valence condition. Examples include aluminum and boron.

In another aspect, the adsorbents of the invention are used in a method for separating an unsaturated hydrocarbon from a mixture by accomplishing adsorption at a first selected pressure and temperature and then accomplishing release or desorption by changing at least one of the pressure and temperature. Preferential adsorption is achieved at a pressure greater than the desorption (release) pressure. Preferential adsorption pressure may be as high as about 35 atmospheres or more; and the desorption pressure may be as low as sub-atmospheric, significant vacuum, 0.01 atmosphere or less. Desirably, the pressure of preferential adsorption is in a range of about 1 atmosphere to about 35 atmospheres; and most desirably about 1 to 2 atmospheres. Desirably, the pressure of release is in a range of about 0.1 atmospheres to about 5 atmospheres; and most desirably in a range of about 0.1 atmospheres to about 0.5 atmospheres. The temperature of preferential adsorption is desirably selected to be in the range of about 0° C. to about 150° C.; more desirably up to about 120° C. and most desirably in a range of about 25° C. to about 80° C. The temperature of release is desirably in a range of about 70° C. to about 250° C., and most desirably, about 100° C. to about 120° C.

The invention provides substantial advantages over conventional methods for separating dienes from a mixture due to the effective and economical process and adsorbents provided by the invention.

Objects, features and advantages of the invention include an improved method for separating diene from a mono-olefin in a mixture, and particularly for separating C4 to C8 diene from a mixture which includes corresponding C4 to C8 mono-olefin. Another objective is to provide new adsorbents used in such new separation method.

These and other objects, features, and advantages will become apparent from the following description of the preferred embodiment, claims, and accompanying drawings.

DESCRIPTION OF THE PREFERRED EMBODIMENTS

Figures 1A, 1B, 1C:
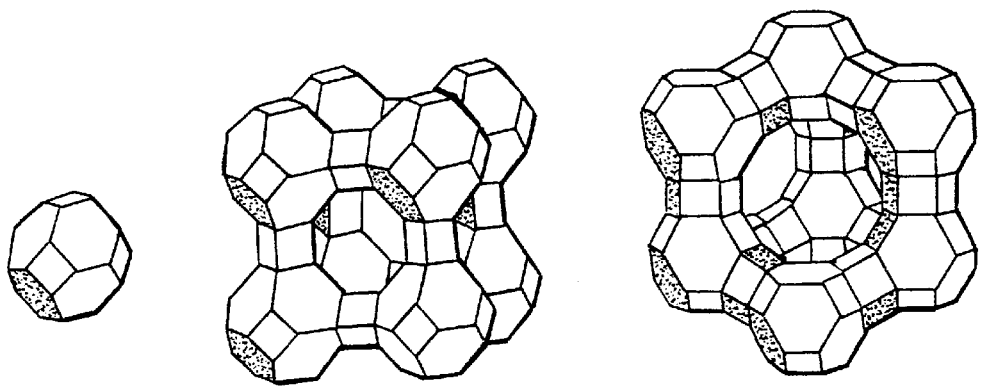
FIG. 1 shows line representations of zeolite structure: (a) solidate cage, or truncated octahedron; (b) type A zeolite "unit cell"; (c) "unit cell" of types X and Y, or faujasite; (d) cation sites in type A (there are eight I, three II, and twelve III sites per unit cell); (e) cation sites in types X and Y (16 I, 32 I', 32 II, 32 II', 48 III, and 32 III' sites per unit cell).

The invention provides improved methods and adsorbents for separating a diene from a mixture which includes such diene. The invention is particularly useful for separating dienes having four to eight carbons from corresponding mono-olefins having four to eight carbons. Improved separation methods are needed due to the close boiling points of the $C_4$ to $C_8$ dienes and their corresponding $C_4$ to $C_8$ mono-olefins. Selected examples are as follows with numerical values being the boiling points in degrees centigrade 1,2- and 1,3-butadiene respectively 10.8 and −4.4; 1-butene, 2-butene cis and trans, respectively −6.3, 3.7 and 0.9; 1,3-, 1,4-, 1,5- and 2,4-hexadiene respectively 73, 65, 59.5, and 80; 1-hexene, 2-hexene cis and trans and 3-hexene cis and trans respectively 63.3, 68.8, 68, 66.4, and 67.1; and 1,7- and 2,6- octadiene at 113-8 and 118-20; and 1-, 2-, 3-, and 4-octene in a range of 121.3–125.6; all according to the 62nd Edition of the CRC Handbook.

In one embodiment, there is provided a process for separating diene from a feed mixture comprising the diene and at least one other unsaturated hydrocarbon compound, where the process comprises contacting the mixture with a diene-selective adsorbent which is an ion-exchanged zeolite. Desirably, the ion-exchanged zeolite is a Y zeolite, X zeolite, and/or low silica X zeolite, (LSX). Most desirably, the exchangeable cationic sites of the zeolite are ion-exchanged with silver cation or copper cation. It is most preferred that the zeolite be a silver zeolite (Ag-zeolite). The character of these zeolites will be described more particularly below. In the case of type LSX zeolite, it is preferred that it have a silicon to aluminum atomic ratio of less than 1.2. It is most preferred that the ratio of Si/Al be about 1.

It is desirable that more than half of the ion exchange sites of the zeolites contain the silver cation in the case of Ag-zeolite. It is preferred that in the case of Ag-zeolite, substantially all of the cation sites are occupied by silver in a +1 oxidation state (+1 valence state). In the case of Cu-zeolite, it is also desirable that more than half of the ion exchange sites contain copper ions. It is also preferred that substantially all of the sites are ion exchanged with copper in the case of copper exchanged zeolites where the copper is in the +1 valence or oxidation state.

In another embodiment, the invention provides a process for causing the separation of diene from one or more other unsaturated hydrocarbons, particularly mono-olefin as described above, using a type A zeolite. In this process the diene is separated from a feed mixture utilizing the type A zeolite having an alkali-metal cation or an alkaline earth metal cation at respective exchangeable cationic sites to cause the selective adsorption of the diene.

Desirably, commercially available 5A zeolite is used. The 5A zeolite contains calcium (Ca) as the major cation. This means that for all the available cation sites of A-zeolite, Ca is found at over half such sites. The minor cation is sodium. Therefore, the 5A zeolite has substantially and essentially all of its cationic sites occupied by Ca and Na, but primarily Ca. This 5A zeolite is also referred to herein as CaA zeolite.

In one embodiment, the type A zeolite optionally contains a mixture of cations besides the alkali metal and alkaline earth metal. Therefore, at some of the cation exchange sites of the zeolite, cations other than +1 and +2 will be present. The nominal formula of this zeolite is $M^{+1}_x Z^{+2}_y A^{+3}_b [(AlO_2)_{12}(SiO_2)_{12}]$ wherein the value of x is 0 to 12 and the value of y is 0 to 6, and the value of b is at minimum zero and at maximum less than the sum of x plus y, provided that:

x+2y+3b is 12. This is believed to provide a mixture of cations in this type A zeolite which is balanced. It is preferred that when the A zeolite contains tri-valent (+3) cations, the atomic amount of such tri-valent is less than the combined amount of the alkali d alkaline metal cations. It is most preferred that in he aforesaid nominal general formula, the alkaline earth metal is primarily Ca, providing Ca-A (5A) zeolite.

The method and adsorbents (sorbents) of the invention are particularly suited for temperature swing adsorption (TSA) and pressure swing adsorption (PSA). The process is effective to separate diene from a mixture containing one or more other unsaturated hydrocarbons and particularly mono-olefin compounds. Before further describing the invention and the use of zeolites of the invention in TSA and PSA processes, more particular description of the physical characteristics of the zeolites of the invention is provided along with preferred ion exchange method.

Zeolites have historically been used as adsorbents due their selectivity. Zeolites selectively adsorb molecules on the basis of the size and the shape of the adsorbate molecule and are therefore called molecular sieves. Zeolites have been known for use in selective adsorption of carbon monoxide and hydrocarbons. Crystalline zeolite Y, zeolite A and zeolite X are described in U.S. Pat. No. 3,130,007; 2,882,243; 3,992,471 and 2,882,244; each of which is incorporated by reference in its entirety. Type 5A zeolite, and type 13X zeolite are described for nitrogen adsorption in U.S. Pat. No. 5,551,257. Types 4A (Na-A) and 5A (Ca-A) zeolites, are described in USPN 3,785,122. Low silica X zeolite (LSX) having Si/Al ratio less than or equal to 1.25, desirably less than or equal to 1.2, and preferably about 1 is described in U.S. Pat. No. 5,268,023. Each of the aforementioned patents is incorporated herein by reference in its entirety. Consistent with the features described in these patents, zeolite characteristics are below excerpted from "Gas Separation Processes" by R. T. Yang (1987, Butterworth Publishers).

Zeolites are crystalline aluminosilicates of alkali or alkali earth elements such as sodium, potassium, and calcium, represented by the stoichiometry:

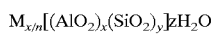

$$M_{x/n}[(AlO_2)_x(SiO_2)_y]zH_2O$$

where x and y are integers with y/x equal to or greater than 1, n is the valence of cation M, and z is the number of water molecules in each unit cell. Unit cells are shown in FIG. 1(b) and (c). The cations are necessary to balance the electrical charge of the aluminum atoms, each having a net charge of −1. The water molecules can be removed with ease upon heat and evacuation, leaving an almost unaltered aluminosilicate skeleton with a void fraction between 0.2 and 0.5. The skeleton has a regular structure of cages, which are usually interconnected by six windows in each cage. The cages can imbibe or occlude large amounts of guest molecules in place of water. The size of the window apertures, which can be controlled by fixing the type and number of cations, ranges from 3 Å to 10 Å. The sorption may occur with great selectivity because of the size of the aperture (and to a lesser extent because of the surface property in the cages)—hence the name molecular sieve.

At least forty species of naturally occurring zeolites have been found. The principal ones are chabazite, (Ca, Na$_2$) Al$_2$Si$_4$O$_{12}$(6 H$_2$O); gmelinite; (Na$_2$, Ca) Al$_2$Si$_4$O$_{12}$(6 H$_2$O); mordenite, (Ca, K$_2$, Na$_2$), Al$_2$Si$_{10}$O$_{24}$(6.66 H$_2$O); levynite, CaAl$_2$Si$_3$O$_{10}$(5 H$_2$O); and faujasite, (Na$_2$, Ca, Mg, K$_2$) OAl$_2$Si$_{4.5}$O$_{12}$(7 H$_2$O). More than 150 types of zeolites have been synthesized; they are designated by a letter or group of letters—Type A, Type X, Type Y, Type ZSM, and so on. The commercial production of synthetic zeolites started with the successful development of low-temperature (25–100° C.) synthesis methods using very reactive materials such as freshly coprecipitated gels or amorphous solids.

The primary structural units of zeolites are the tetrahedra of silicon and aluminum, SiO$_4$ and AlO$_4$. These units are assembled into secondary polyhedral building units such as cubes, hexagonal prisms, octahedra, and truncated octahedra. The silicon and aluminum atoms, located at the corners of the polyhedra, are joined by a shared oxygen. The final zeolite structure consists of assemblages of the secondary units in a regular three-dimensional crystalline framework. The ratio Si/Al is commonly one to five. The aluminum atom can be removed and replaced by silicon in some zeolites, thereby reducing the number of cations; and the cations can also be exchanged. The inner atoms in the windows are oxygen. The size of the windows depends, then, on the number of oxygen atoms in the ring—four, five, six, eight, ten, or twelve. The aperture size, as well as the adsorptive properties, can be further modified by the number and type of exchanged cations. A description of the structures will be given only for the zeolites important in gas separation, Type A and Type X and Y. (See Table I).

Figure 1D:
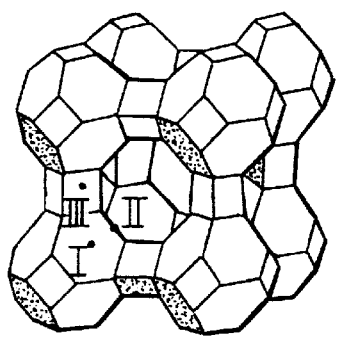

Type A. The structural unit in Type A zeolite, as well as in Types X and Y, is the truncated octahedron, shown in FIG. 1(a). This unit is also called sodalite cage, as sodalite is formed by directly fusing the four-member rings of the units. The four-member rings of the sodalite units can also be linked through four-member prisms, as shown in FIG. 1(b), which is type A zeolite. The unit cell of Type A zeolite, as shown in this figure, contains 24 tetrahedra, 12 AlO$_4$ and 12 SiO$_4$. When fully hydrated, 27 water molecules are contained in the central cage or cavity of the unit cell, and in the eight smaller sodalite cages. The free diameter in the central cavity is 11.4 Å, which is entered through six eight-member oxygen-ring apertures with a minimum diameter of 4.4 Å. There are twelve negative charges to be balanced by cations in each unit cell. The most probable locations for the cations are indicated in FIG. 1(d). Type I is at the center of the six-member ring, thus at one of the eight corners of the cavity. Type II is at the eight-member aperture, directly obstructing the entrance. Type III is near the four-member ring inside the cavity. Type A zeolites are synthesized in he sodium form, with 12 sodium cations occupying all eight sites in I and three sites in II, plus one site in III. This is the commercial Type 4A zeolite, with an effective aperture size of 3.8 Å. The sodium form can be replaced by various other cations or by a hydrogen ion. The commercial Type 3A zeolite is formed by exchanging Na$^+$ with K$^+$, resulting in a smaller effective aperture size due to the larger K$^+$. The aperture size of the sodium form can also be increased by exchanging Na$^+$ with Ca$^+$ or Mg$^{+2}$, since 2 Na$^+$ are replaced by one bivalent cation. The form of the exchanged Ca$^{+2}$ or Mg$^{+2}$ is Type 5A with rather unobstructed and larger apertures.

Figure 1E:
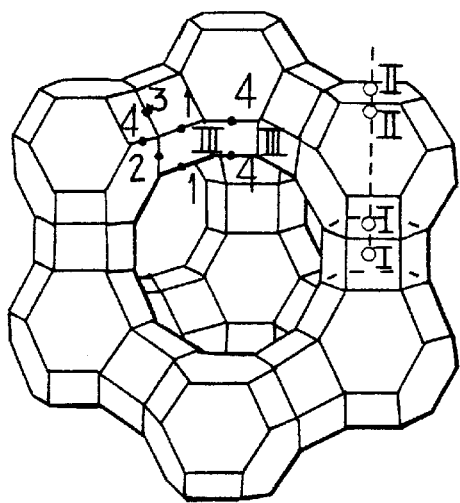

Types X and Y. The skeletal structure of Types X and Y zeolites are the same as that of the naturally occurring faujasite. The sodalite units are linked through six-member prisms, as shown in the unit cell in FIG. 1(c). Each unit cell contains 192 (Si, Al)O$_4$ tetrahedra. The number of the aluminum ions per unit cell varies from 96 to 77 for Type X zeolite, and from 76 to 48 for Type Y zeolite. This framework has the largest central cavity volume of any known zeolite, amounting to about 50% void fraction in the dehydrated form. A unit cell, when fully hydrated, contains approximately 235 water molecules, mostly in the center cavity. The aperture is formed by the twelve-member oxygen rings with a free diameter of approximately 7.4 Å. Three major locations for the cations are indicated in FIG. 1(e). The locations are: center of the six-member prism (I) and opposite to I in the sodalite cage (I'); similar to I and I' but further from the central cavity (II and II'); and at the twelve-member aperture (III and III'). The commercial 10X zeolite contains $Ca^{+2}$ as the major cation, and Na+ is the major cation for 13X zeolite. The distribution of $Na^+$, $K^+$, $Ca^{+2}$, other cations, and $H_2$ in X and Y zeolites. The BET surface area measured with $N_2$ for zeolites falls in the range between 500 and 800 $m^2/g$.

In one aspect, adsorbents of the invention, as described below, achieve selective adsorption by means of the π-complexation mechanism. Separation by π-complexation is a subgroup of chemical complexation where the mixture is contacted with a second phase, which contains a complexing agent. The advantage of chemical complexation is that the bonds formed are stronger than those by van der Waals forces alone, so it is possible to achieve high selectivity and high capacity for the component to be bound. At the same time, the bonds are still weak enough to be broken by using simple engineering operations such as raising the temperature or decreasing the pressure.

The π-complexation generally pertains to the main group (or d-block) transition metals, that is, from Sc to Cu, Y to Ag, and La to Au in the periodic table. These metals or their ions can form the normal σ bona to carbon and, in addition, the unique characteristics of the d orbitals in these metals or ions can form bonds with the unsaturated hydrocarbons (olefins) in a nonclassic manner. This type of bonding is broadly referred to as π-complexation, and has been considered for gaseous hydrocarbon separation and purification using cumbersome liquid solutions.

It is known, that for many olefin separations, conventional π-complexation sorbents did not provide a large working capacity for the target olefin. The examples below show that the sorbents of the invention have superior selectivity for 1,3-butadiene adsorption. The examples show the new adsorbents (sorbents) usable with preferred PSA and TSA processes for very effective diene separation.

The PSA process is effectively usable with the new sorbents of the invention. Here, multiplicity of periodic steady states is an important aspect of cyclic adsorption process. For pressure swing adsorption (PSA), multiple steady states exist for a fixed set of operating conditions, over a particular range of one or more of these operating variables (i.e., bifurcation variables). The final stable state depends only on the initial condition (i.e., the perturbation variables).

There are a variety of commercial applications in which component separation is conducted by pressure swing adsorption (PSA) and temperature swing adsorption (TSA). Other less commonly used processes are volume swing adsorption and concentration swing adsorption. The most commonly described are PSA and TSA systems.

In PSA processing, a feed mixture containing a more readily adsorbable component and a less readily adsorbable component is passed through an adsorbent bed capable of selectively adsorbing the more readily adsorbed component at an upper adsorption pressure. The less readily adsorbable component passes through the bed and is recovered from the discharge end of the bed. Then, the bed is depressurized to a lower desorption pressure for desorption of the more readily adsorbable component, and its removal from the bed. Thereafter, the cyclic operation resumes.

In temperature swing adsorption processing, the adsorbent is exposed to the feed mixture for a period of time during which the more readily adsorbed component is adsorbed. Thereafter the flow of the feed is shut off from the adsorbent bed and the adsorbent is exposed to a purge fluid, typically a gas, which strips the adsorbed component from the bed and regenerates the bed for further use. In TSA, the adsorbed component is driven off from the bed by heating the adsorbent in the regeneration state. Therefore, the temperature of desorption is higher than the temperature of the adsorption portion of the cycle. Details of PSA and TSA adsorption will not be repeated here, as they may be found in the following United States Patents, each of which is incorporated by reference herein, in its entirety: 5,268,023; 5,551,257; 5,554,208; 5,672,196; 5,672,196.

Ion exchange of zeolite is easily accomplished by mixing the zeolite in an aqueous solution of the metal salt. The metal of the salt is the metal to be exchanged into the cationic site. The concentration of the solution is varied according to the desired level of ion exchange. The ion exchanged zeolite is then removed by filtration from the aqueous solution and washed free of the soluble salts. This batch ion exchange is widely used due to its simplicity. Essentially complete ion exchange can be achieved by repeating the same procedure several times. By such repeated treatment, over 90% of the exchangeable cationic sites are ion-exchanged with $Ag^+$. Preferably, over 95% of such sites are ion exchanged. The same high level of exchange is obtainable with the copper ion exchange. The Ag zeolites of the invention were prepared by ion exchanging with a solution of $AgNO_3$ containing five times the cationic exchange capacity of the zeolites. This was done to assure complete ion exchange. The Cu-zeolites of the invention were prepared by ion exchanging with a solution of $CuCl_2$ or $Cu(NO_3)_2$, followed by reduction of $Cu^{+2}$ to $Cu^{+1}$.

The following examples show new sorbents for the challenging separation of removing trace amounts of dienes (50 PPM) from a normal alpha olefin (NAO) stream. The sorbents of the examples below demonstrate operability for a pressure swing adsorption (PSA) or temperature swing adsorption (TSA) mode.

The sorbents of the example were pre-selected based on two types of interactions: kinetic and weak chemical complexation. The first type of interaction derives from the molecular sieving effects of certain substrates such as zeolites or carbon molecular sieves (CMS). However, zeolites were mainly considered for this application due to their high Henry's Law region adsorption. For this approach, the small differences in the kinetic diameters of mono-olefin are exploited. This is accomplished by exchanging cations of various sizes into the pore aperture of type A zeolite.

Due to the olefinic nature of the components involved in the examples, weak chemical and complexation-based sorbents that have demonstrated the capabilities of adsorbing olefin over paraffins are not necessarily suited for diene separation from mono-olefin. In the separation of diene from mono-olefin, both adsorbates are olefinic in character. Dienes are known to have three arrangements of the double bonds. Double bonds that alternate with single bonds are said to be conjugated; double bonds that are separated by more than one single bond are said to be isolated. A third, less important class of dienes contain cumulated double bonds, that is, double bonds adjacent one another and known as allenes. One of the most common dienes is 1,3-butadiene. Its boiling point is −4.4° C. and very close to 1-butene (−6.3° C.). Separation of these two compounds is very difficult due to their close boiling points. The major difference between the two is the conjugate diene nature of 1,3-butadiene. Since 1,3 butadiene is present in such low concentrations, the bond between the sorbate and the adsorbent must be very strong in order to adsorb significant amounts of butadiene at such low partial pressures.

In the examples, it was shown that the properties of the sorbent can be tailored by selecting specific cations and substrates. When dealing with bulk separations, high amounts adsorbed at low pressures are usually not desired, and are usually avoided because they limit the working capacity of the adsorbent. However, for this particular application, a high Henry's law constant is required. Therefore, zeolite-based sorbents are a good candidate for substrates. It is shown that $Ag^+$ exchange Y zeolite has high affinity for olefins at very low pressures. Therefore, the examples focus on using zeolitic materials such as Type A, X, or Y, ion exchange with $Cu^+$ or $Ag^+$ cations to carry out the separation of 1, 3-butadiene from 1-butene. It should be noted that the separation of the conjugated butadeine from butene is merely exemplary. The processes described below are also applicable to separate other dienes such as hexadiene and octadiene from mixtures containing hexene and octene. The temperatures and pressure given below are also exemplary.

Depending on the chosen conditions, the separation is accomplished in the gas phase, the liquid phase or some combination thereof, including for example, saturated gas. It should be noted that the butadiene and butene of the examples share common chemical characteristics with other diene/mono-olefin combinations described earlier. Therefore, the effectiveness of the invention in separating all such stated combinations is apparent.

The sorbents described in the examples below contained various cations included in high surface area substrates. The dispersion of cations was accomplished using ion exchange. The chemistry of ion exchange in zeolites is well documented. See U.S. Pat. No. 2,882,243, 2,882,244 and 5,268,023, each of which is incorporated herein in its entirety. All exchanges were performed similarly. They involved vacuum filtering and washing of the zeolite with deionized water. Compared to the original cation exchange capacity (CEC), each solution contained 10-fold cation equivalents. This procedure ensured 100% exchange. For A (Linde), LSX (low silica X, UOP), and Y (Strem Chemicals) zeolites, the starting forms contain $Na^+$. The zeolites used were powder form (binderless). Prior to use the samples were calcined in vacuo at 350° C.

In the examples below, the hydrocarbons used as the adsorbates were 1,3 butadiene (CP grade, Matheson), 1-butene (CP grade) and helium (pre-purified grade, Metro Welding 99.995%) was used as the carrier gas and as the regeneration gas. The gasses were used without further purification. Isotherms and uptake rates were measured utilizing both a Shimadzu TGA-50 microbalance system following well known procedures. For low pressure data (<0.05 atm), a Micrometrics ASAP 2010 pore size distribution analyzer was utilized. This system is capable of accurately measuring pressures in a range between $1\times10^{-7}$–1.25 atm. While one can obtain data at very low pressures with the Micromeritics ASAP 2010, this is very time consuming. The Shimadzu TGA-50 thermogravimetric analyzer is used to screen potential sorbents. Also, measurements were made at two temperatures (25° C., 70° C.) in order to obtain isosteric heats of adsorption. The overall diffusion time constants, $D/R^2$, were calculated from the uptake curves measured from a stepped pressure increment from 0.0 to 0.6 atm by well known methods and assumptions.

EXAMPLE 1

Pre-screening of Y-type Zeolites for 1,3-Butadiene Selectivity

The framework structure of LSX and Y-type zeolites resembled that of the naturally occurring faujasite (see FIG. 1). The pores of these zeolites are made of 12-member oxygen rings. They have an aperture size of about 8.1 Å. They only differ in the ratios of Si/Al. This ratio determines the number of cations per unit cell and therefore has a significant effect on the adsorption properties. Y-type zeolites contain between 56 and 76 cation sites, respectively. It is because of the properties mentioned above that these zeolites were selected as substrates. The large size aperture facilitates the diffusion of large molecules such as 1,3-butadiene and 1-butene. Also, the large number of cation sites available for exchange with $Cu^{1+}$ or $Ag^{1+}$ helps increase the adsorption capacity.

Figure 2:
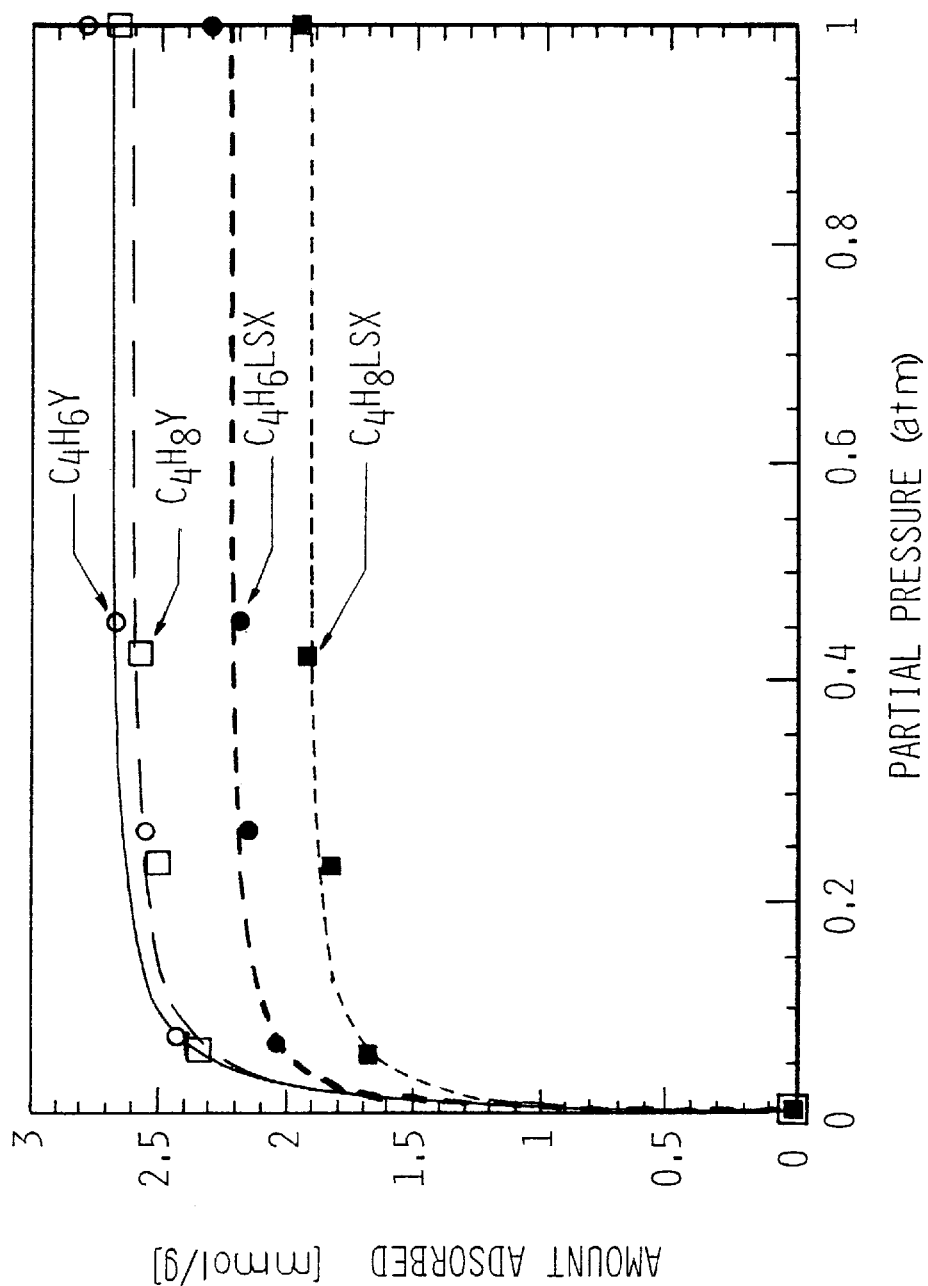
FIG. 2 shows the pure-component equilibrium isotherms of 1,3-$C_4H_6$ and 1-$C_4H_8$ on NaY and NaLSX type zeolites at 70° C.
Figure 3:
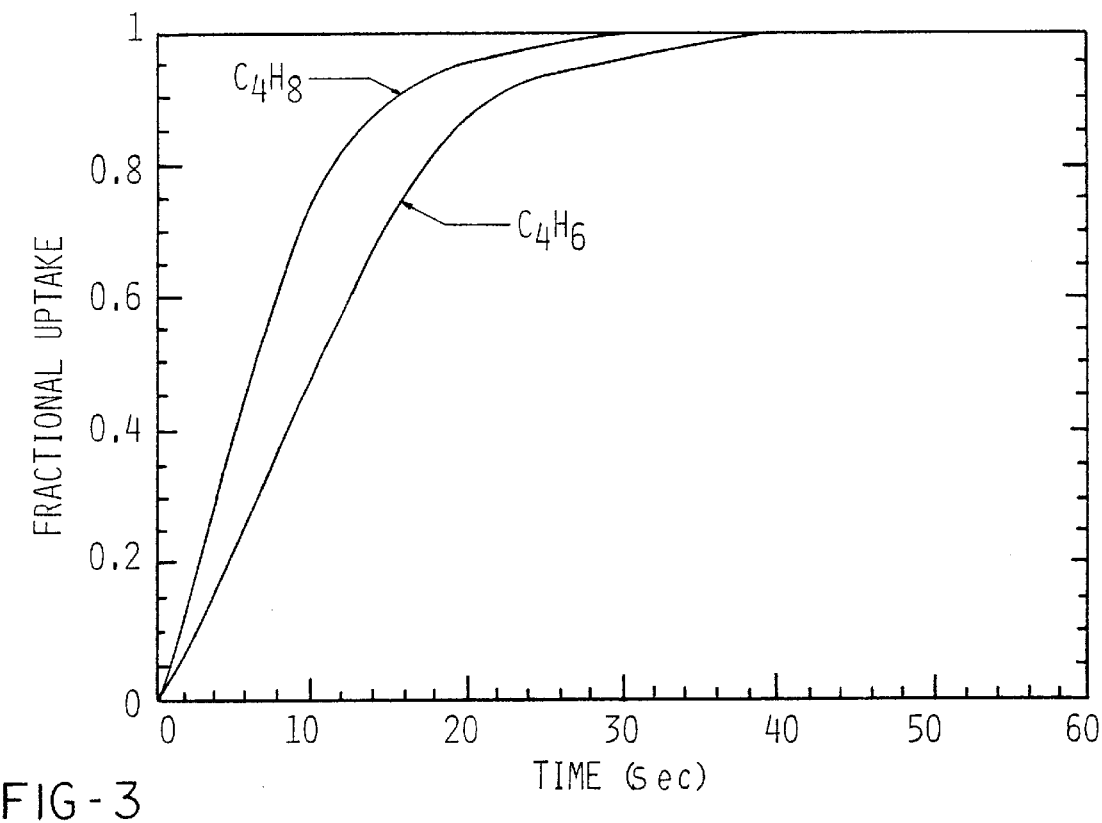
FIG. 3 shows uptake curves for 1,3-$C_4H_6$ and 1-$C_4H_8$ on NaY-type zeolites.

The pure-component equilibrium isotherms of 1,3-$C_4H_6$ and 1-$C_4H_8$ on NaY and NaLSX type zeolites at 70° C. are shown in FIG. 2. The partial pressures ranged from 0.06 to 1 atm. While these pressures are outside the range of interest for 1,3-$C_4H_6$, they are useful for screening potential substrates and for determining capacities for 1-$C_4H_8$. The equilibrium data was fitted with the Langmuir isotherm model. The equilibrium amounts of 1,3-$C_4H_6$ and 1-$C_4H_8$ adsorbed at 70° C. at 1 atm on NaY zeolite were 2.80 and 2.69 mmol/g respectively. This equals about 36 molecules of 1,3-$C_4H_6$ and 34 molecules of 1-$C_4H_8$ per unit cell of NaY-type zeolite. Uptake curves for 1,3-$C_4H_6$ and 1-$C_4H_8$ on NaY-type zeolites are shown in FIG. 3. They were obtained by performing a step change in pressure from 0–0.06 atm. Both components diffused very fast. Complete uptake was achieved within 50 seconds. This was due to the very large pore aperture size of the NaY zeolite, about 7.4 Å. Diffusion time constants, $D/R^2$, were calculated by fitting experimental data with the solution of the diffusion equation for spherical particles as described by Karger and Ruthven in 1992. The values of $D/R^2$ obtained for 1,3-$C_4H_6$ and 1-$C_4H_8$ at 70° C. were $7.85\times10^3$ and $5.76\times10^3$ 1/s, respectively. The ratio of the diffusivities is rather small ($\approx 1.3$) for kinetic separation application. However, one favorable characteristic of Y-type zeolite is its relatively high Henry's Law constant. This indicates that the Y-type zeolites have good affinity for C4's and are also good candidates for C6's and C8's.

EXAMPLE 2

Selectivity of Ion-Exchanged Y-Zeolite for 1,3-Butadiene

Figure 4:
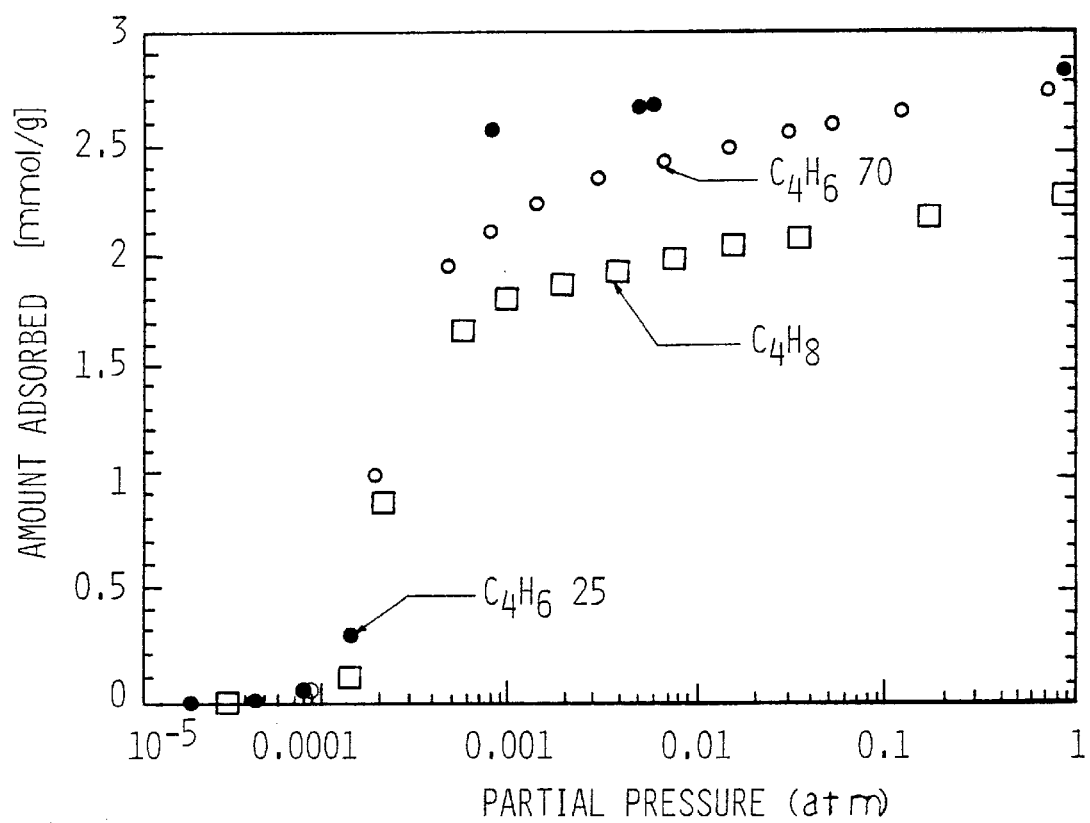
FIG. 4 shows the pure component equilibrium isotherms for 1,3-$C_4H_6$ and 1-$C_4H_8$ AgY zeolite at 70° C. and 25° C.

As per Example 1, Y-type zeolites have a very high affinity for C4's at low pressures. Therefore, this material is a good substrate for 1-butene purification, and also for hexene and octene purification. In order to increase the affinity of the NaY zeolite for 1,3 butadiene, the $Na^{1+}$ cation was fully exchanged by $Ag^{1+}$ which is capable of π-complexation with olefinic compounds. The pure component equilibrium isotherms for 1,3-$C_4H_6$ and 1-$C_4H_8$ AgY zeolite at 70° C. and 25° C. are shown in FIG. 4. The partial pressure in this isotherm ranged from $1\times10^{-5}$ atm to 1 atm. The lower end of the scale corresponds to a concentration equal to 10 PPM. The equilibrium amounts of 1,3-$C_4H_6$ and 1-$C_4H_8$ at 70° C. and 1 atm were measured at 2.8 and 2.3 mmol/g. These results are very interesting because at high loadings it appears that exchanging Na with Ag had lesser effect on the amounts of 1,3-$C_4H_8$ adsorbed.

Low pressure 1,3-$C_4H_6$ and 1-$C_4H_8$ adsorption data on AgY type zeolite at 70° C. is also shown in FIG. 4. In this Figure, it can be observed that at 70° C. the amount of 1,3-$C_4H_6$ adsorbed at 50 PPM was about 0.5 mmol/g. This amount is somewhat small. The amount of 1,3-$C_4H_6$ is improved by decreasing the adsorption temperature or increasing pressure. Equilibrium adsorption isotherms for 1,3-$C_4H_6$ on AgY type zeolite are shown in FIG. 4 also. Although 1,3-$C_4H_6$ adsorption did not improve in the region of importance, $1 \times 10^{-5}$ to $5 \times 10^{-5}$ (10–50 PPM), there was an increase in adsorption at higher loadings.

The lack of 1,3-$C_4H_6$ adsorbed in the low pressure range with the decrease in temperature could be attributed to equipment error. It is possible for the Micormeritics ASAP 2010 to cut off adsorption before uptake completion for a particular pressure point if the system is too slow diffusing. This possible error was corrected and a new equilibrium isotherm for 1,3-$C_4H_6$ on AgY zeolite was included as per an example which follows below.

EXAMPLE 3

Confirmation of Selectivity

Figure 5:
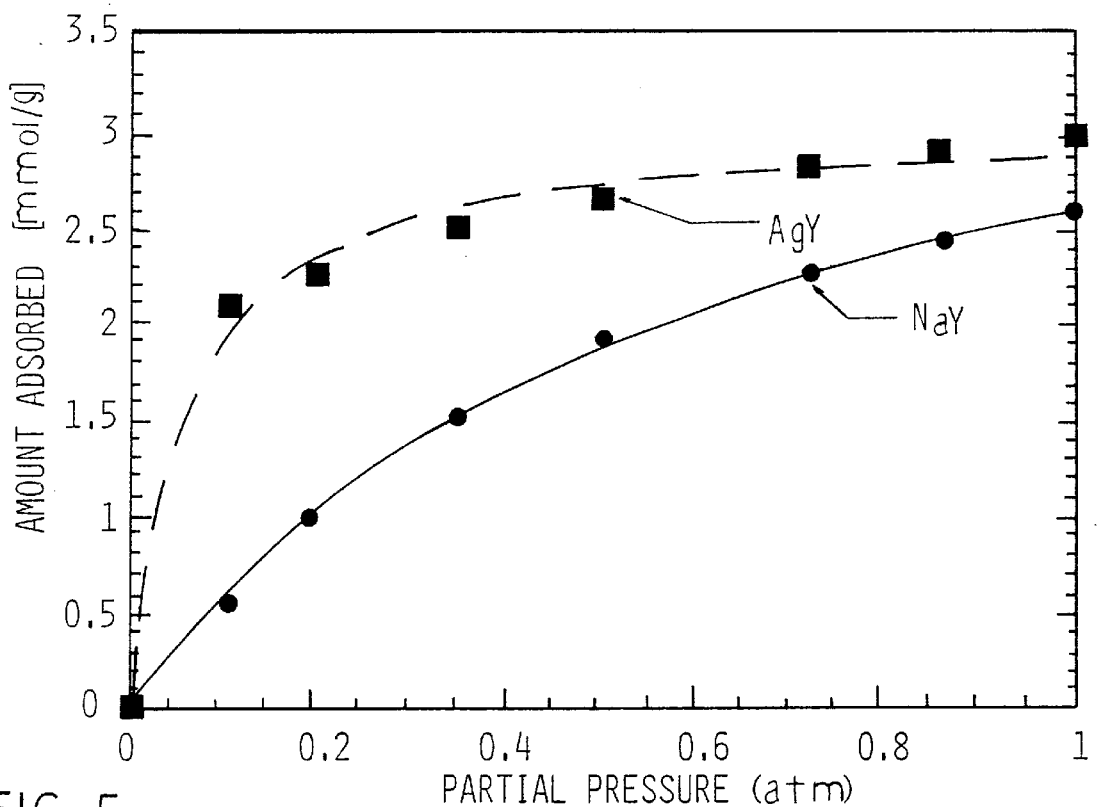
FIG. 5 shows the equilibrium isotherms of $C_2H_4$ on NaY and AgY type zeolites at 70° C.

In order to confirm the π-complexation activity of the sorbent, it was tested with $C_2H_4$ at 70° C. The equilibrium isotherms of $C_2H_4$ on NaY and AgY type zeolites at 70° C. are shown in FIG. 5. In this figure, the effect of π-complexation can be clearly observed at low pressures. However, at higher pressures, this effect is somewhat diminished. This phenomenon could be attributed to a filling of the pore cavity of Y-type zeolite. However, for this particular application, the behavior of the sorbent at high loadings is not important. It is the low pressure behavior of the sorbent which is critical for this particular purification-type application.

EXAMPLE 4

A-Type Zeolite Selectivity for 1,3-Butadiene

The structural unit of Type A zeolite is the sodalite cage. The unit cell of Type A zeolite contains 12 $AlO_4$ and 12 $SiO_4$ (see FIG. 1). There are twelve negative charges to be balance by cations in each cell unit. The free diameter in the central cavity is 11.4 Å (Yang, 1987). Access to the pores is restricted by 8-membered oxygen rings with a free aperture of 4.3 Å in the unobstructed $Ca^{2+}$ (5A) form. This can be reduced to 3.8 Å by exchanging with $Na^+$ and to 3.0 Å by exchanging with $K^+$. It is this wide variation of pore sizes and smaller cavity size that makes type A zeolites desirable for butadiene separation.

Figure 6:
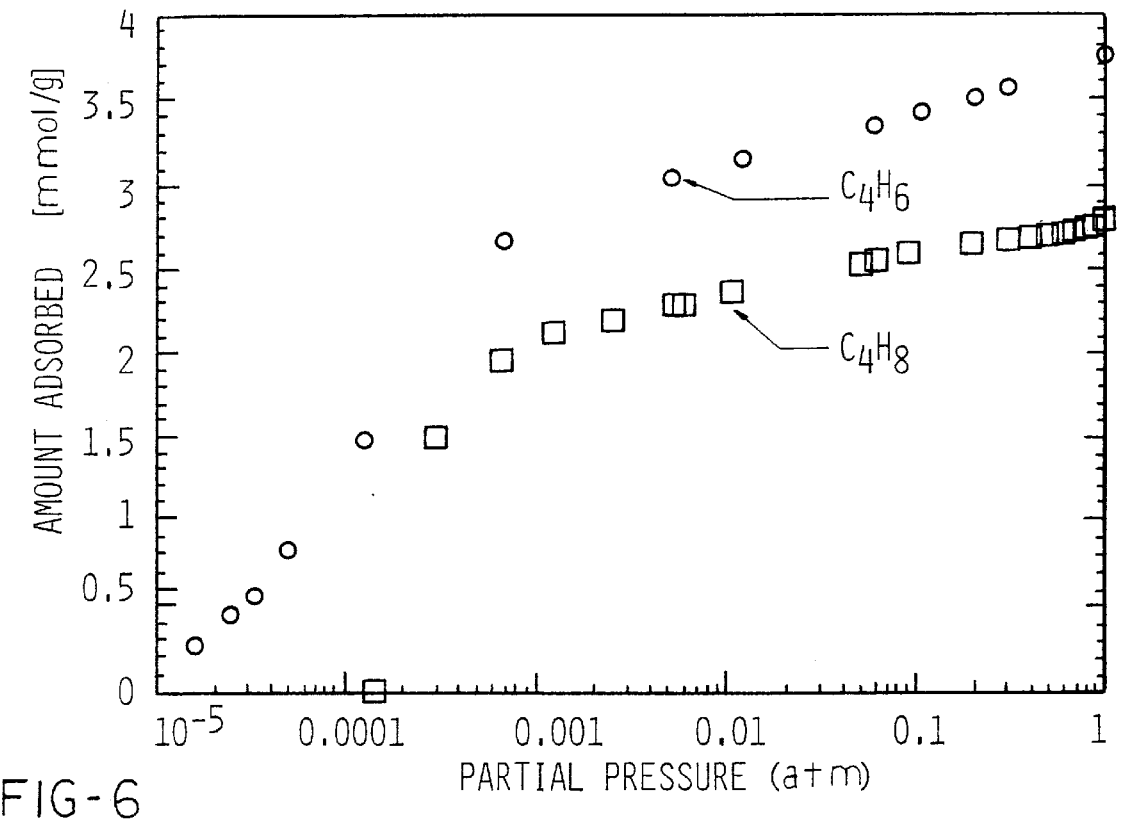
FIG. 6 shows low pressure equilibrium isotherms for 1,3-$C_4H_6$ and 1-$C_4H_8$ on 5A zeolite at 25° C.

Commercially available (5A) Zeolite from Linde was tested. Low pressure equilibrium isotherms for 1,3-$C_4H_6$ and 1-$C_4H_8$ on 5A at 25° C. are shown in FIG. 6. Equilibrium amounts of 1,3-$C_4H_6$ and 1-$C_4H_8$ at 1 atm were measured at 3.8 and 3.3 mmol/g, respectively. The low pressure adsorption of this material was excellent. At a concentration of 50 PPM, this material adsorbed 0.8 mmol/g of 1,3 $C_4H_6$. The working capacity of this sorbent between 50 and 10 PPM is also excellent. This was measured at approximately 0.7 mmol/g.

EXAMPLE 5

5A Zeolite and 5A Ion-Exchanged Zeolite Selectivity

Figure 7:
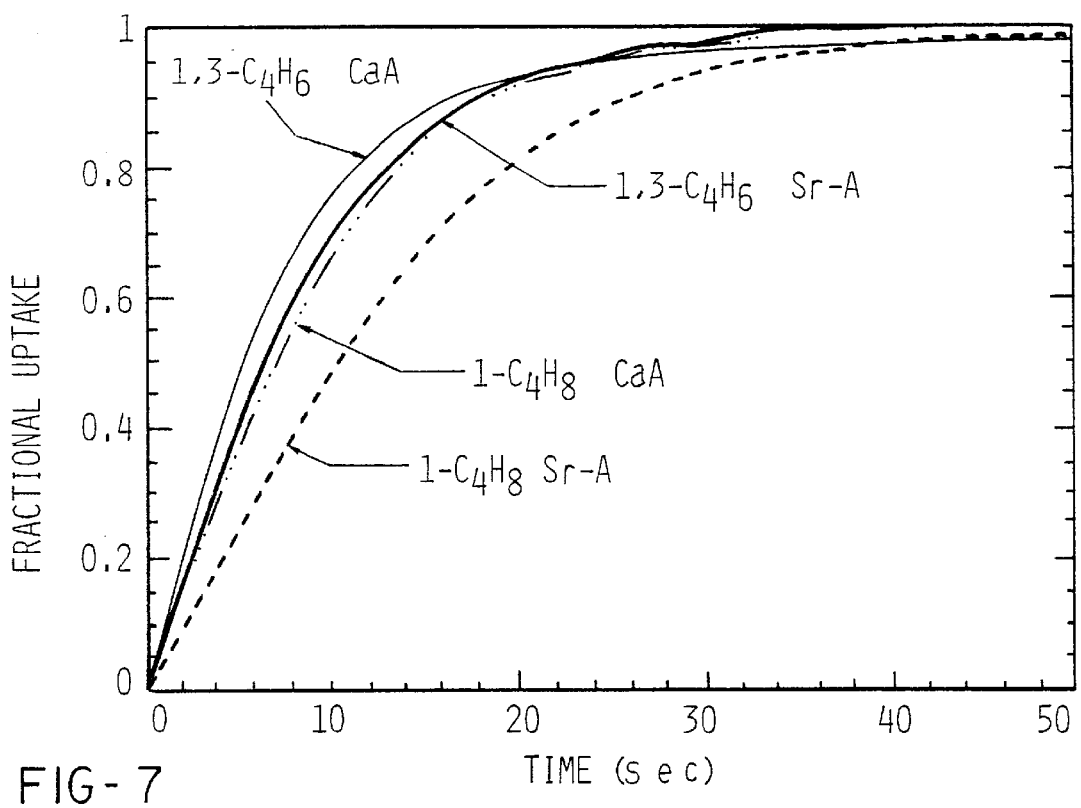
FIG. 7 shows uptake curves for 1,3-$C_4H_6$ and 1-$C_4H_8$ on Sr exchanged 5A and 5A zeolites measured at 70° C.

This example builds on the success of 5A type zeolite in adsorbing 1,3-$C_4H_6$ at very low loadings. Here, the focus was to reduce 1-$C_4H_8$ adsorption. As mentioned earlier, one of the strategies to synthesize a sorbent for this application was to use kinetic or steric effects to separate 1,3-$C_4H_6$ (butadiene) from 1-$C_4H_8$ (butene). Therefore, it is possible to limit 1-$C_4H_8$ adsorption by hindering its uptake or completely excluding it from the pore structure. This was accomplished by exchanging $Ca^+$ cations in the pores of Type A zeolite with several cations of various sizes. The pure component equilibrium isotherm for 1,3-$C_4H_6$ and 1-$C_4H_8$ on Sr exchanged 5A at 25° C. are shown in FIG. 7. The pressure in this isotherm ranged from $1 \times 10^{-5}$ to 1 atm. Equilibrium adsorption amount for 1,3-$C_4H_6$ on Sr exchanged 5A at 25° C. and 1 atm was measured at 3.1 mmol/g. Although this sorbent showed excellent capacity at high loadings (≈1 atm), it did not adsorb significant amounts of 1,3-$C_4H_6$ in the 10–50 PPM regime. Uptake curves for 1,3-$C_4H_6$ and 1-$C_4H_8$ on Sr exchanged 5A and 5A were measured at 70° C. and are shown in FIG. 7. The values of $D/R^2$ for 1,3-$C_4H_6$ and 1-$C_4H_8$ on CaA were calculated at $1.07 \times 10^2$ and $7.30 \times 10^{-3}$ 1/s, respectively. Diffusion time constants were also measured on Sr exchanged 5A and were calculated at $8.55 \times 10^{-3}$ and $4.06 \times 10^{-3}$ 1/s, respectively. Due to the larger radius of $Sr^{2+}$ over $Ca^{2+}$ (1.12 vs. 0.99 Å), a small reduction in 1-$C_4H_8$ uptake rates is observed. However, the reduction in 1-$C_4H_8$ uptake is not significant enough for a kinetic separation scheme. If the ion exchange is performed with the next larger cation, $Ba^{2+}$, with a radius of 1.34 Å, the uptakes of both adsorbents are severely hindered. Therefore, it is questionable whether hindrance of 1-$C_4H_8$ access to the pore structure of A type zeolites using simple ion exchange techniques is possible without also blocking 1,3-$C_4H_6$. The small difference in kinetic diameter between the two molecules is problematic.

Figure 8:
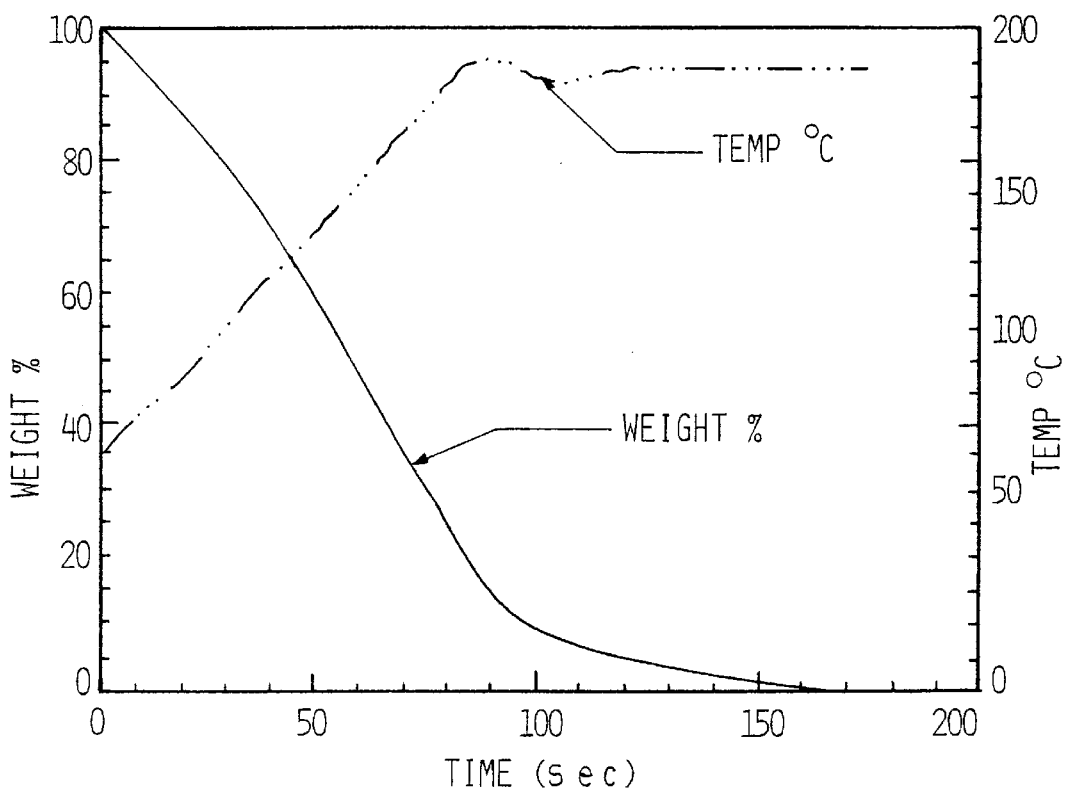
FIG. 8 shows desorption curve for temperature driven release of 1,3-$C_4H_6$ from 5A zeolite.

Desorption experiments were carried out on 1,3-$C_4H_6$ on 5A zeolite at 70° C. However, these experiments were performed in the Shimadzu TG-50 TGA. Therefore, they do not include data below 0.06 atm. Equilibrium amounts of 1,3-$C_4H_6$ on 5A Zeolite at 70° C. and 1 atm were measured at 2.81 mmol/g. After desorption, at 1 atm, the sample was exposed to a helium stream at 70° C. to regenerate it. However, this procedure only removed 1.23 mmol/g which left 1.58 mmol/g of 1,3-$C_4H_6$. This final amount was removed by heating the sample to 180° C. in the presence of helium. A desorption curve is shown in FIG. 8. As per the above examples, success has been achieved with 5A zeolite for 1,3-butadiene separation. It is not clear yet the reason for the success of 5A and the lesser performance of Sr exchanged 5A which is very similar structurally. The pore size of this zeolite determines its effectiveness for C6 and C8 separation.

EXAMPLE 6

1,3 Butadiene/1-Butene Separation: π-Complexation Effects

In previous examples there is shown 1,3-butadiene ($C_4H_6$) adsorption on AgY zeolite at various temperatures. These examples did not include data to directly compare the effects of π-complexation on $C_4H_6$ adsorption. This example includes a direct comparison by measuring $C_4H_6$ adsorption on the sodium-exchanged type Y zeolite (NaY). It is known that the sodium cation is not capable of π-complexating with olefins. A comparison involving AgA and CaA (5A) was not used because of the dominance of kinetic effects in the AgA system. The pore size of AgA lies in the range between 3A and 4A type zeolites.

Figure 9:
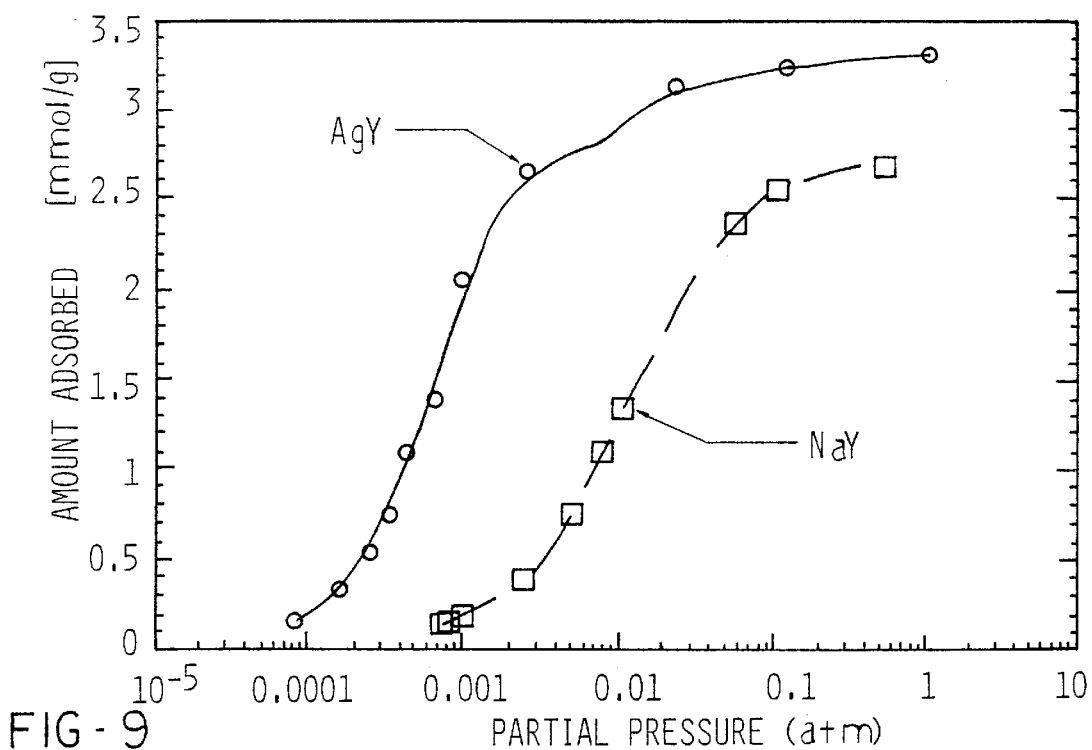
FIG. 9 shows equilibrium adsorption isotherms for $C_4H_6$ on AgY and NaY at 120° C.

Equilibrium adsorption isotherms for $C_4H_6$ on AgY and NaY at 120° C. are shown in FIG. 9. The effect on π-complexation is observed in the equilibrium amounts of $C_4H_6$ adsorbed on AgY and NaY at 1 atm which were measured at 3.3 and 2.6 mmol/g, respectively. However, the adsorption of $C_4H_6$ at 50 PPM of saturation pressure of 1-Butene ($C_4H_8$) at 120° C. ($1.1\times101^{-3}$ atm) is a more significant parameter. Using this parameter, the effects of π-complexation are more significant. The adsorption amounts of $C_4H_6$ at 50 PPM on AgY and NaY were measured at 2.7 and 0.3 mmol/g, respectively. The working capacity of the sorbents in the range of 50 to 10 PPM ($1.1\times10^{-3}$–$2.2\times10^{-4}$ atm) was calculated at 2.35 and 0.2 mmol/g, respectively. When the working capacities of the sorbents are calculated, the superior performance of π-complexation sorbents becomes evident.

EXAMPLE 7

Butadiene-Butene Separation

Figure 10:
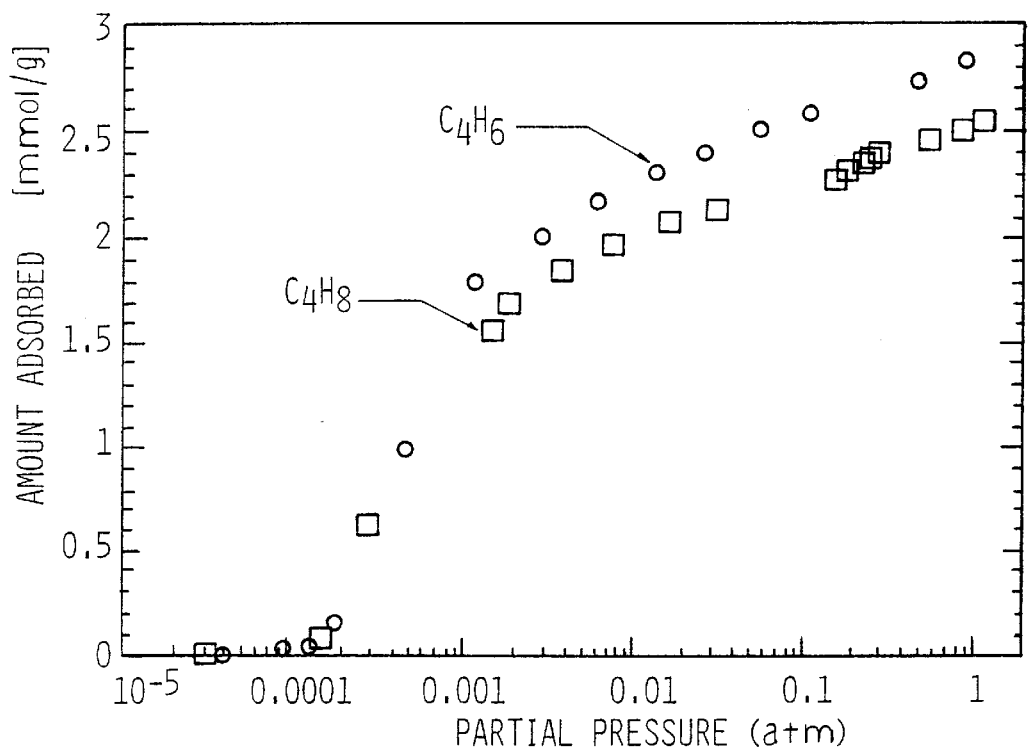
FIG. 10 shows low pressure equilibrium isotherms for 1,3-$C_4H_6$ and 1-$C_4H_8$ on 5A at 70° C.

In the earlier examples, the isotherms of 1-butene and butadiene on 5A zeolite at 25° C. were shown. Added isotherms were measured at 70° C. The isotherms are shown in FIG. 10. The amounts adsorbed are lower at 70° C. More significantly, the heel of the isotherm for butadiene is shifted toward a higher partial pressure. Fortunately, however, the amount adsorbed is quite high at a butadiene partial pressure of 50 ppm of 10 atm (i.e., the saturation pressure of butene at 70° C. The amount is approximately 1 mmol/g. The amount adsorbed at 10 ppm of 10 atm is nearly zero. Hence 5A zeolite is an attractive sorbent for this selective removal of diene at 70° C. (at a total pressure of 10 atm). The polar nature of the surface of the zeolite is though to contribute to the separation.

TABLE I

LSX, Y and A zeolite nominal chemical formulas

| | |
|---|---|
| AgLSX | $Ag_{96}[(AlO2)_{96}(SiO2)_{96}]$ |
| AgY | $Ag_{54}[(AlO2)_{54}(SiO2)_{138}]$ |
| CaA | $Ca_6[(AlO2)_{12}(SiO2)_{12}]$ |
| CuLSX | $Cu_{96}[(AlO2)_{96}(SiO2)_{96}]$ |
| CuY | $Cu_{54}[(AlO2)_{54}(SiO2)_{138}]$ |
| Mixed Metal A | $M^{+1}{}_xZ^{+2}{}_yA^{+3}{}_b[(AlO2)_{12}(SiO2)_{12}]$ (x + 2y + 3b = 12) |

Note: In X-type zeolites, the $AlO_2/SiO_2$ ratio is greater than 54/138; and the total valence of the cations is equal to the number of $AlO_2$ units.

The invention provides substantial advantages over conventional methods for separating diene from a mixture. The adsorbents and methods of the invention are useful for purifying mono-olefin from a mixture which includes mono-olefin and diene. The adsorbents and methods can be used to purify either the diene or to purify the mono-olefin. The adsorbents and methods as exemplified in the examples demonstrate particular effectiveness for removing a diene from a mixture comprising the diene and one or more mono-olefins. The examples show effective separation results using gas-phase separation at the pressures and temperatures stated therein. The adsorbents and processes are demonstrated for a saturated 1-butene (olefin) stream, which is contaminated with 1,3-butadiene (diene), typically at one weight percent or less. The separation in this case may include both gas and liquid phase selective adsorption due to the saturated nature of the 1-butene olefin stream. The processes described herein are described with reference to separation of C4 to C8 diene from a C4 to C8 mono-olefin. The physical characteristics of the adsorbents result in very effective separation as demonstrated by the examples. Depending on the chosen conditions, the separation is accomplished in the gas phase, the liquid phase or some combination thereof, including, for example, saturated gas. For the reasons described above, the adsorbents are also considered to be useful for separation of other dienes, that is C4 to C10 dienes from C4 to C10 mono-olefins. Beyond C10 the process is also thought to be applicable, for example, C12 diene/C12 mono-olefin separation. However, the selectivity and economic benefits are expected to decline for the higher hydrocarbon mono-olefin/diene separation.

The invention provides good results at operating temperatures and pressures that are not extreme. Good results are achievable at pressures on the order of sub-atmospheric (i.e., 0.01 to 0.1 atm) to moderately high (i.e. 20 to 30 atm) and in a pressure swing adsorption method. Good results are achievable at temperatures from ambient or a desired feed temperature (i.e. 0 to 25° C.) and up to moderately high (i.e. 250° C.), and in a temperature swing adsorption method. With the adsorbents of the invention, temperature swing or pressure swing adsorption processes are usable for effective separation between dienes and mono-olefins. This is demonstrated by the very effective purification of butenes, by removing 1,3-butadiene at concentrations above 20 ppm to final concentration below 10 ppm. Therefore, the invention provides a very attractive solution to the problem of selective adsorption of trace amounts of diene to separate diene from a mixture.

While this invention has been described in terms of certain embodiments thereof, it is not intended that it be limited to the above description, but rather only to the extent set forth in the following claims.

The embodiments of the invention in which an exclusive property or privileged is claimed, are defined in the following claims:

What is claimed is:

1. A process for separating a diene from a mixture including said diene, said process comprising the step of:

contacting said mixture with an adsorbent which preferentially adsorbs said diene, thereby producing a non-adsorbed component and a diene-rich adsorbed component, wherein said adsorbent comprises an ion-exchanged zeolite selected from the group consisting of zeolite X, zeolite Y, zeolite LSX, and mixtures thereof, said zeolite having exchangeable cationic sites, and essentially all cationic sites of said ion-exchanged zeolite contain silver cation or copper cation, and wherein the preferential adsorption occurs by π-complexation.

2. The process of claim 1 wherein said mixture comprises at least one mono-olefin having as many carbon atoms as said diene.

3. The process of claim 2 wherein said diene is selected from the group consisting of butadiene, hexadiene, octadiene and mixtures thereof; and said mono-olefin is selected from the group consisting of butene, hexene, octene and mixtures thereof.

4. The process of claim 2 wherein said mono-olefin is butene and said diene is butadiene.

5. The process of claim 2 wherein said mono-olefin is hexene and said diene is hexadiene.

6. The process of claim 2 wherein said mono-olefin is octene and said diene is octadiene.

7. The process of claim 2 wherein said mixture comprises said mono-olefin in a gaseous state and saturated with said diene.

8. The process of claim 1 wherein said LSX zeolite has a silicon to aluminum (Si/Al) atomic ratio of less than or equal to 1.2.

9. The process of claim 8 wherein said ratio is one.

10. The process of claim 1 wherein said X and Y zeolites respectively have a silicon to aluminum ratio of 1:1 and 1000:1.

11. The process of claim 1 wherein essentially all cationic sites of said ion-exchanged zeolite contain said silver cation.

12. The process of claim 1 wherein essentially all cationic sites of said ion-exchanged zeolite contain said copper cation.

13. A process of separating a diene selected from the group consisting of butadiene, hexadiene, octadiene and mixtures thereof from a mixture including said diene, said process comprising the steps of:

contacting said mixture with an adsorbent which preferentially adsorbs and releasably retains said diene at a selected temperature and pressure, thereby producing anon-adsorbed component and a diene-rich adsorbed component, wherein said adsorbent comprises an ion-exchanged zeolite selected from the group consisting of zeolite X, zeolite Y, zeolite LSX, and mixtures thereof, said zeolite having cation exchange sites, essentially all cationic sites of said ion-exchanged zeolite contain silver cation or copper cation, and wherein the preferential adsorption occurs by $\pi$-complexation; and then changing at least one of said pressure and temperature to thereby release said diene-rich component from said adsorbent.

14. The process of claim 13 wherein the selected pressure of preferential adsorption is a first pressure, and the pressure of release is a second pressure less than said first pressure.

15. The process of claim 14 wherein said first pressure is in a range of about 1 atmosphere to about 35 atmospheres.

16. The process of claim 14 wherein said first pressure is in a range of about 1 atmosphere to about 2 atmospheres.

17. The process of claim 14 wherein said second pressure is in a range of about 0.01 atmosphere to about 5 atmospheres.

18. The process of claim 14 wherein said second pressure is in a range of about 0.1 atmosphere to about 0.5 atmospheres.

19. The process of claim 13 wherein the selected temperature of preferential adsorption is a first temperature, and the temperature of release is a second temperature greater than said first temperature.

20. The process of claim 19 wherein said first temperature is in a range of about 0° C. to about 150° C.

21. The process of claim 19 wherein said first temperature is in a range of about 25° C. to about 80° C.

22. The process of claim 19 wherein said second temperature is in a range of about 70° C. to about 250° C.

23. The process of claim 19 wherein said second temperature is in a range of about 100° C. to about 120° C.

24. A process for separating 1,3-butadiene from a mixture comprising 1,3-butadiene and at least one other $C_4$ unsaturated compound, said process comprising the step of contacting said mixture with an adsorbent which preferentially adsorbs said 1,3-butadiene, said adsorbent comprising a silver or copper ion-exchanged zeolite selected from the group consisting of zeolite Y, zeolite X, low silica X zeolite (LSX), and combinations thereof;

wherein said zeolite comprises a plurality of cation exchangeable sites, and essentially all cationic sites of said ion-exchanged zeolite contain silver or copper cations, and wherein the preferential adsorption occurs by $\pi$-complexation.

25. The process of claim 24 wherein essentially all of said cationic sites contain silver cations.

26. The process of claim 24 wherein essentially all of said cationic sites contain said copper cations.

\* \* \* \* \*